United States Patent [19]

Barberet et al.

[11] Patent Number: Plant 5,432

[45] Date of Patent: Apr. 9, 1985

[54] CARNATION NAMED LONTOCIA

[75] Inventors: Nicole Barberet; Yves Ducloux, both of Antibes, France

[73] Assignee: Laboratoire de Physiologie Vegetale de La Londe, Antibes, France

[21] Appl. No.: 512,727

[22] Filed: Jul. 11, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of carnation particularly distinguished by its generally orange colored flowers, the petals of which are lightly streaked with a deep red, the flowers being of medium size and borne on erect and rigid but rather brittle stems of medium length. The blooms are produced abundantly during the blooming periods of Spring and Fall and this plant has a vigorous and upright growth habit with moderately abundant foliage and very few branches.

1 Drawing Figure

BACKGROUND OF THE NEW PLANT

This new carnation variety was developed by us during the course of breeding efforts carried on at La Londe, Les Maures, France, since 1977 with the object of producing new varieties having nice color, good quality of flower production and stem, and good growth habits. Our new plant originated as a seedling resulting from our cross of Stock Plants 75 J 12 and 70 R 5, both unnamed and unpatented, and this new plant was selected by us from the seedlings produced by that crossing because it appeared to have good character of flower color and growth habit that would be advantageous in the cut flower market. We asexually reproduced the discovery plant at La Londe, by means of cuttings, and because the first reproduction of the parent plant exhibited the novel and desirable characteristics of the discovery plant, we carried on the propagation of this new variety through several successive generations at La Londe and thereby determined that the distinctive and advantageous characteristics of the parent plant were fully retained from generation to generation and appear to be firmly fixed.

DESCRIPTION OF THE DRAWING

Our new variety of carnation plant is illustrated by the accompanying photographic drawing which shows, in full color, a typical arrangement of buds, partially opened flowers and full blooms, the colors depicted being as nearly true to those herein specified as it is reaonably possible to obtain by conventional photographic procedures.

DESCRIPTION OF THE NEW PLANT

The following is a detailed description of our new carnation cultivar based upon observations of greenhouse grown plants made at La Londe, France, in the Spring of 1983, the color designations specified herein being according to The R.H.S. Colour Chart of The Royal Horticultural Society of London, England.

THE PLANT

Origin: Seedling.

Parentage:

*Seed parent.*—Stock Plant No. 75 J 12 (unpatented).

*Pollen parent.*—Stock Plant No. 70 R 5 (unpatented). These unnamed varieties are individually identified in our permanent records and are contained in our collection of carnation plants maintained at La Londe, France, for breeding purposes.

Classification:

*Botanic.*—*Dianthus caryophyllus.*

*Commercial.*—Standard Carnation.

Form: Tall, leafy bush.

Height: Averaging about 78 cm. at eight months.

Main stem:

*Length.*—Less than 15 cm. due to pinching.

Branching character: Very few branches but at least four stems emitted near the ground.

Growth habit: Vigorous, upright and rigid with good strength.

Foliage:

*Quantity.*—Moderately abundant.

*Number of leaves.*—More than 120.

*Leaf size.*—Average at the seventh node, about 13.5 cm. long and 9 mm. wide.

*Shape.*—Linear with curved to rolled margins and acuminate tips.

*Texture.*—Leathery.

*Color.*—Upper side — 189A and 189B. Under side — 189A and 189B.

*Ribs and veins.*—Hardly noticeable.

*Rachis.*—Hardly noticeable.

THE BUD

Shape: Ovoid.

Size: Medium, averaging about 2.2 cm. in diameter and about 4 cm. in length.

Rate of opening: Normal for carnations.

Color of petals:

*When sepals first divide.*—Lightly clearer than 32D.

*When petals begin to unfurl.*—32D And 33C.

Sepals: Joined at the lower part and having a generally ovate character at the upper end with sharply pointed apex.

*Number.*—Five. Sepals are hooded over the bud and curl back when the flowers open.

*Color.*—Inside — Greenish White. Outside — 144B and 145C.

*Striae.*—Longitudinal.

Calyx:
*Shape.*—Bell-shaped; almost cylindrical.
*Size.*—Large, broad and medium long.
*Splitting.*—Very rarely.
*Aspect.*—Smooth
Flower stem:
*Length.*—About 66 cm.
*Character.*—Erect and rigid but brittle.
*Color.*—189A And 137B.

THE FlOWER

Blooming habit: Recurrent and profusely in the midseasons of Spring and Fall.
Size of bloom: Medium.
*Diameter.*—About 8.1 cm. in average.
*Depth.*—Average about 6.2 cm.
Borne: Singly.
Shape:
*When bloom first opens.*—With high center.
*When bloom matures.*—Dome shaped.
Petalage:
*Number.*—Averaging about 64.
*Arrangement.*—Imbricated.
*Form.*—Fan-shaped with rounded angles and finely serrated outer edges.
*Texture.*—Soft.
*Appearance.*—Satiny.
*Color.*—Outer Petal: Body — 33C streaked with 46B. Base — Yellowish Green. Reverse side — 32D streaked with 45C. Inside Petal: Body — 33C streaked with 46B. Base — Yellowish Green. Reverse side — 32D streaked with 45C.
Petaloids:
*Number.*—More than 17.
*Size.*—Smaller than petals.
*Color.*—The same as the petals.

Flower stem:
*Length.*—About 66 cm.
*Character.*—Upright and of good strength.
*Color.*—189A and 137B.
Fragrance: Very light.
Persistence: The flowers hang on and dry.
Lasting quality:
*As a cut flower.*—At least ten days in vase keeping.

REPRODUCTIVE ORGANS

Stamens:
*Number.*—Various, from 9 to 17.
*Arrangement.*—Around the pistils.
*Anthers.*—Size: Less than 4 mm. Color: Whitish
*Filaments.*—Color — Whitish.
Pistils:
*Number.*—In general, four.
*Styles.*—Color — Greenish White.
*Stigmas.*—Color — Lightly Pinkish White.
Characteristic of ovaries: Strongly ribbed and of brownish color.

When compared with the similar flower "Tangerine", our new plant has a deeper color and a few red streaks not seen in "Tangerine". The flower of our new plant has a more important doubleness and a far less splitting of the calyx. Also, the stem of our new plant is not very branched.

We claim:

1. A new and distinct carnation cultivar, substantially as herein shown and described, characterized in particular by the shrimp red color of its blooms which are streaked with union jack red; and by its vigorous and rigid growth habit, moderately abundant foliage and relatively few branches.

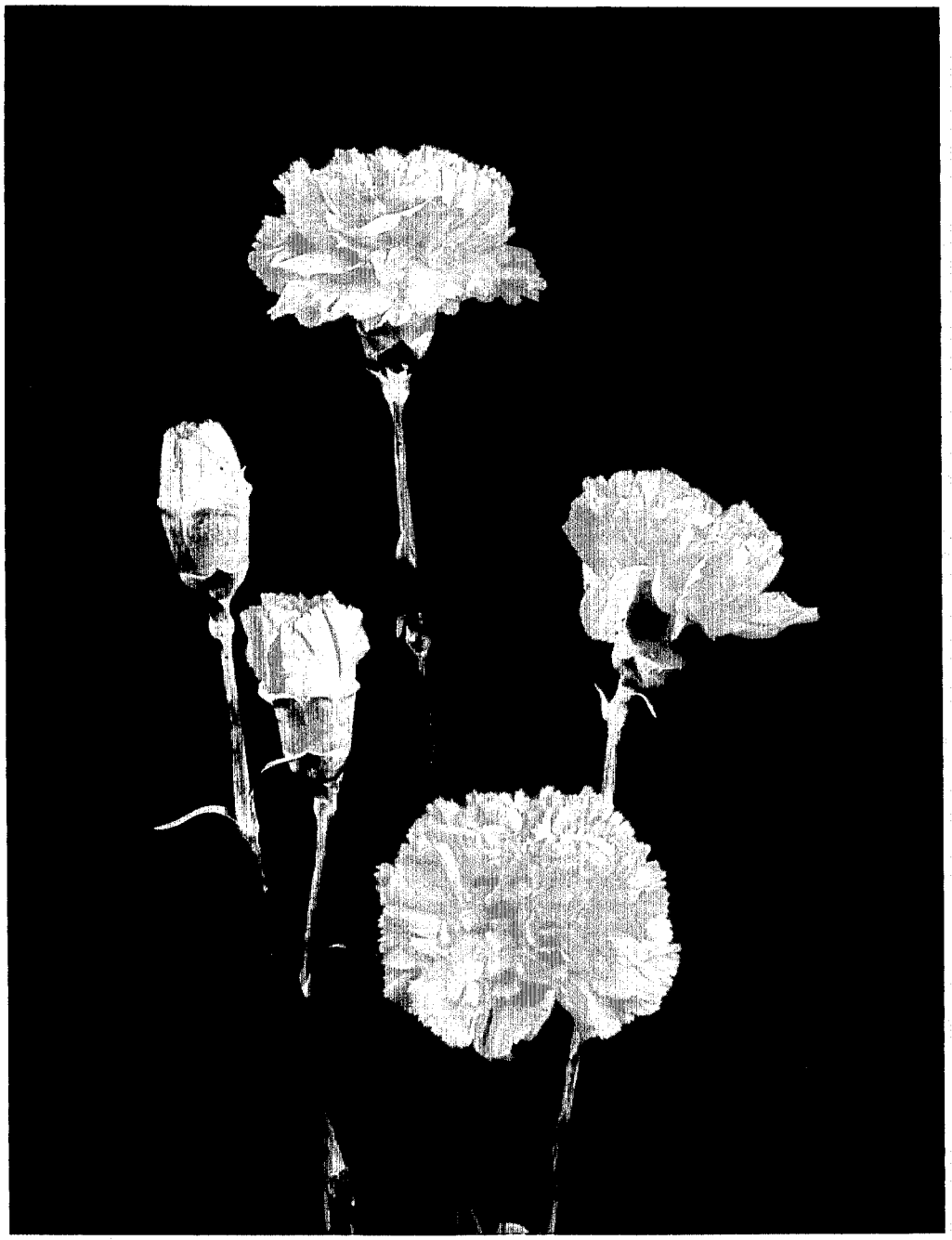

* * * * *